United States Patent [19]

Brown et al.

[11] Patent Number: 5,131,534
[45] Date of Patent: Jul. 21, 1992

[54] SUTURE DISPENSER

[75] Inventors: David L. Brown, Wallingford; Stanley J. Malinowski, Guilford, both of Conn.

[73] Assignee: United States Surgical Corporation, Norwalk, Conn.

[21] Appl. No.: 638,370

[22] Filed: Jan. 7, 1991

[51] Int. Cl.⁵ .................................. A61B 17/06
[52] U.S. Cl. ........................... 206/63.3; 206/339
[58] Field of Search ............... 242/137, 137.1, 138, 242/141, 146; 206/63.3, 339, 380

[56] References Cited

U.S. PATENT DOCUMENTS

| | | | |
|---|---|---|---|
| D. 263,505 | 3/1982 | Black | 206/63.3 |
| D. 265,972 | 8/1982 | Black | 206/63.3 |
| 443,812 | 12/1890 | Barber | 206/63.3 |
| 2,376,151 | 5/1945 | Karle | 206/63.3 |
| 2,376,152 | 5/1945 | Karle | 206/303.3 |
| 2,893,548 | 7/1959 | Carver, Jr. et al. | 206/63.3 |
| 2,938,624 | 5/1960 | Runkel et al. | 206/63.3 |
| 3,095,159 | 6/1963 | Stacy et al. | 206/63.3 |
| 3,112,825 | 12/1963 | Hammond et al. | 206/63.3 |
| 3,185,299 | 5/1965 | Trainer | 206/63.3 |
| 3,231,215 | 1/1966 | Horine | 206/63.3 |
| 3,301,393 | 1/1967 | Regan, Jr. et al. | 206/63.3 |
| 3,361,382 | 1/1968 | Converse | 206/63.3 |
| 3,376,973 | 4/1968 | Granowitz et al. | 206/63.3 |
| 3,481,690 | 12/1969 | Edgworth | 206/63.3 |
| 3,495,703 | 2/1970 | Calabrese | 206/63.3 |
| 3,545,608 | 12/1970 | Berger et al. | 206/63.3 |
| 3,648,949 | 3/1972 | Berger et al. | 206/63.3 |
| 3,749,238 | 7/1973 | Taylor | 206/63.3 |
| 3,815,843 | 6/1974 | Fortune | 206/63.3 |
| 3,901,244 | 8/1975 | Schweizer | 206/63.3 X |
| 4,084,692 | 4/1978 | Bilweis | 206/63.3 |
| 4,706,843 | 11/1987 | Thornton | 242/138 X |
| 4,925,073 | 5/1990 | Tarrson et al. | 242/138 X |

FOREIGN PATENT DOCUMENTS

| | | |
|---|---|---|
| 662417 | 4/1963 | Canada . |
| 0228965 | 7/1987 | European Pat. Off. . |
| 1195425 | 11/1959 | France . |
| 2240712 | 3/1975 | France . |
| 2283974 | 4/1976 | France . |
| 2277565 | 6/1976 | France . |
| 2308724 | 11/1976 | France . |
| 2320253 | 3/1977 | France . |
| 2324315 | 4/1977 | France . |
| 2346483 | 10/1977 | France . |
| 2358164 | 2/1978 | France . |
| 2427415 | 12/1979 | France . |
| 2460126 | 1/1981 | France . |
| 2592024 | 6/1987 | France . |
| 624072 | 8/1961 | Italy . |

Primary Examiner—Paul T. Sewell
Assistant Examiner—Jacob K. Ackon, Jr.
Attorney, Agent, or Firm—Peter G. Dilworth; Rocco S. Barrese; Thomas R. Bremer

[57] ABSTRACT

A reel-type surgical suture dispenser features an extension member on the suture reel receptacle, there being positioned upon the extension member an upwardly projecting suture-retaining slotted member which facilitates dispensing of the suture and retaining thereon the terminal section of a length of suture withdrawn from the reel.

12 Claims, 4 Drawing Sheets

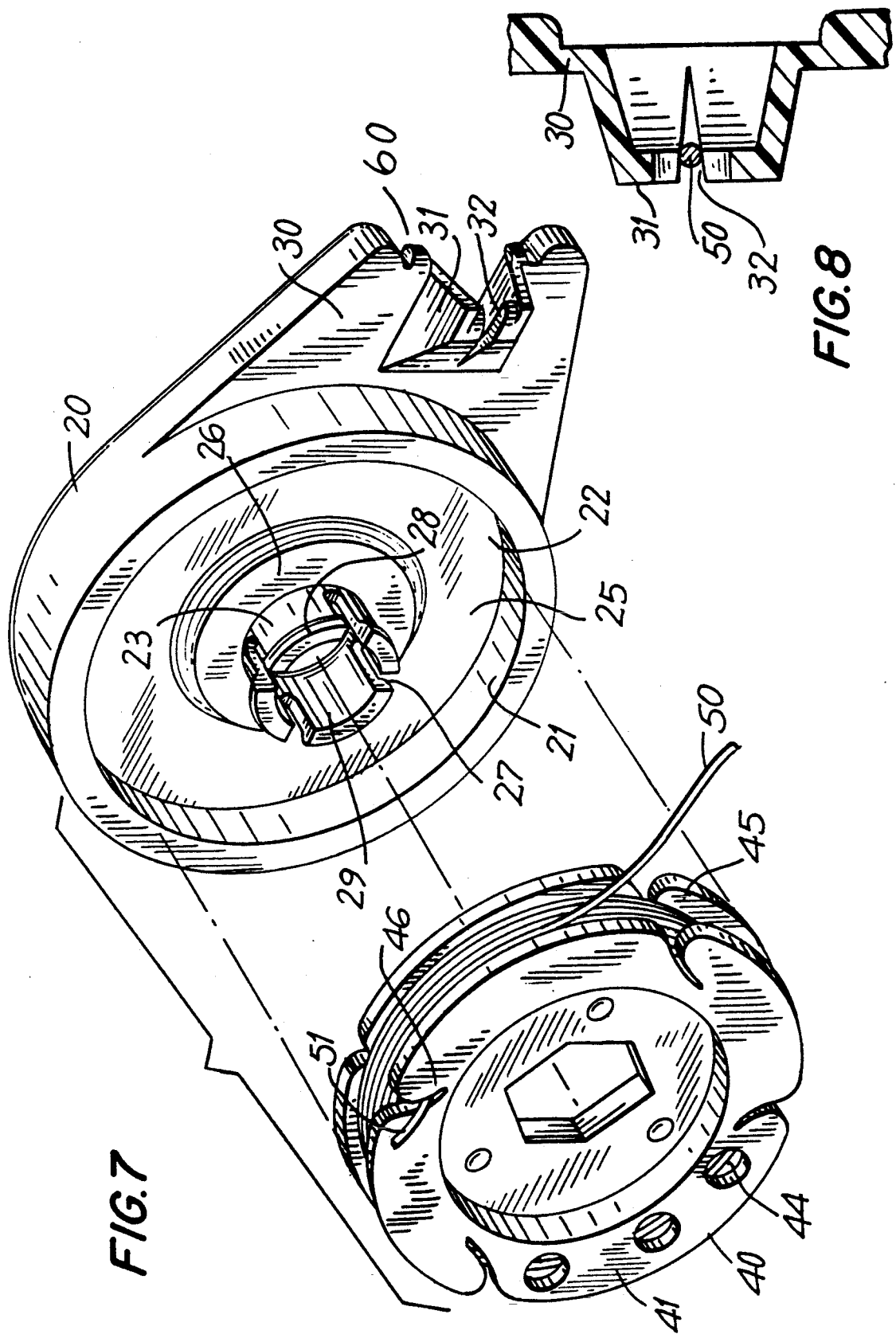

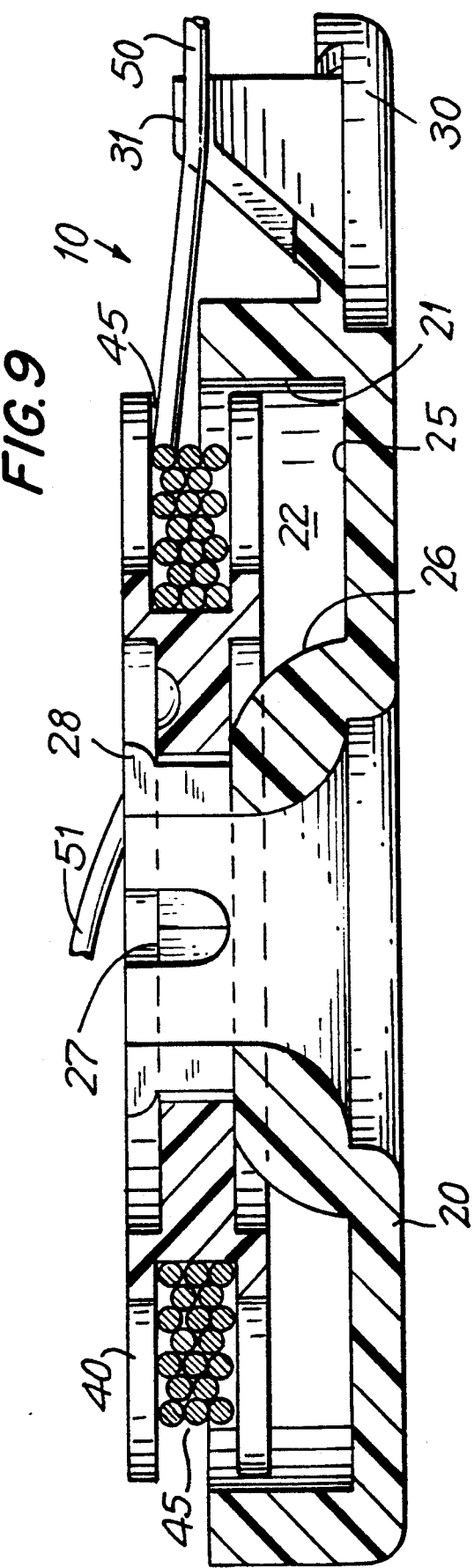
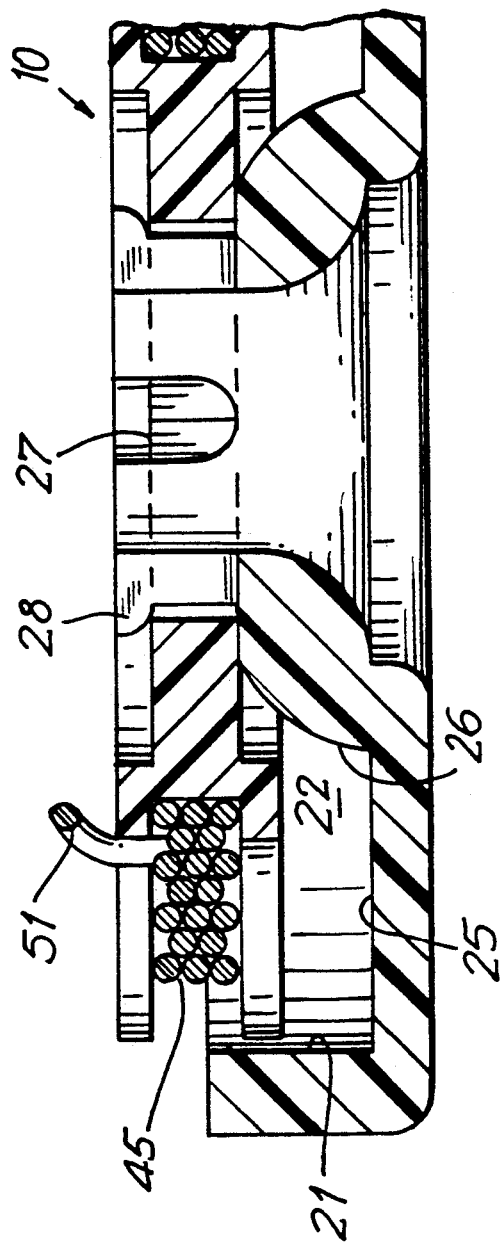

SUTURE DISPENSER

BACKGROUND OF THE INVENTION

This invention relates to a surgical suture dispenser and, more particularly, to a reel-type suture case for storing and dispensing desired lengths of suture.

A surgical ligature, or suture, when packaged as a coil in a protective tube has a tendency to kink upon being unwound. Kinking requires that the suture be straightened out prior to its use, a requirement which prolongs the surgical operation. To obviate this difficulty, hand-held suture dispensers featuring a reel for storing a quantity of suture have been developed to provide a desired length of suture which, being free of kinks or other irregularities, can be used immediately without the need for straightening or similar preparative manipulation. Suture reel dispensers of known construction are described, e.g., in U.S. Pat. Nos. 2,376,151, 2,376,152, 2,938,624, 3,095,159, 3,112,825, 3,185,299, 3,376,973, 3,545,608, 3,648,949, 3,749,238, 3,815,843 and 4,084,692, U.S. design Pat. Nos. 263,505 and 265,972, Canadian Pat. No. 662,417, European patent application No. 228,965, French Pat. Nos. 2,240,712, 2,277,565, 2,283,974, 2,308,724, 2,320,253, 2,324,315, 2,346,483, 2,358,164, 2,427,415, 2,460,126 and 2,592,024 and Italian Pat. No. 624,072.

In many of these known suture reel dispensers, as the suture is withdrawn from the reel, it rubs against the case in which the suture reel is rotatably seated and when a desired length of suture has been played out, the suture is held by a retaining member which is approximately flush with the wall of the case. This arrangement, in addition to resulting in suture rubbing can make the suture more difficult to grasp and/or withdraw from the dispenser. See, e.g., U.S. Pat. No. 4,084,692 for a suture dispenser of this type.

SUMMARY OF THE INVENTION

In accordance with the present invention, in a reel-type suture dispenser possessing a cylindrically shaped receptacle, a suture-dispensing reel rotatably seated within the receptacle and an extension member connected to a section of the receptacle, an improvement is provided which comprises an upwardly projecting suture-retaining slotted member positioned upon the extension member.

Provision of the upwardly projecting suture-retaining slotted member on the extension of the receptacle provides easier access to the suture for its more convenient removal from the dispenser. In addition, the elevated slotted member can reduce and even eliminate the incidence of contact of the suture with the receptacle which is encountered in known types of suture dispensers, e.g., as described in U.S. Pat. No. 4,084,692 referred to above. This avoidance of contact of the suture with its receptacle is advantageous in as much as it removes a potential point of abrasion which could deleteriously affect the suture and/or the coating material which is commonly applied thereto.

BRIEF DESCRIPTION OF THE DRAWINGS

In FIGS. 1–10 in which like reference numerals refer to like elements throughout:

FIG 1 is a perspective view of a fully assembled suture dispenser in accordance with the invention;

FIGS. 2–6 are, respectively, top (FIG. 2), right side (FIG. 3), front (FIG. 4), rear (FIG. 5) and bottom (FIG. 6) views of the suture dispenser;

FIG. 7 is an exploded perspective view of the suture dispenser;

FIG. 8 is a cross sectional view of the upwardly projecting suture-retaining slotted member component of the suture dispenser; and, FIGS. 9 and 10 are, respectively, side elevation and front elevation views in cross section of the suture dispenser.

DESCRIPTION OF THE PREFERRED EMBODIMENTS

Figure 1:
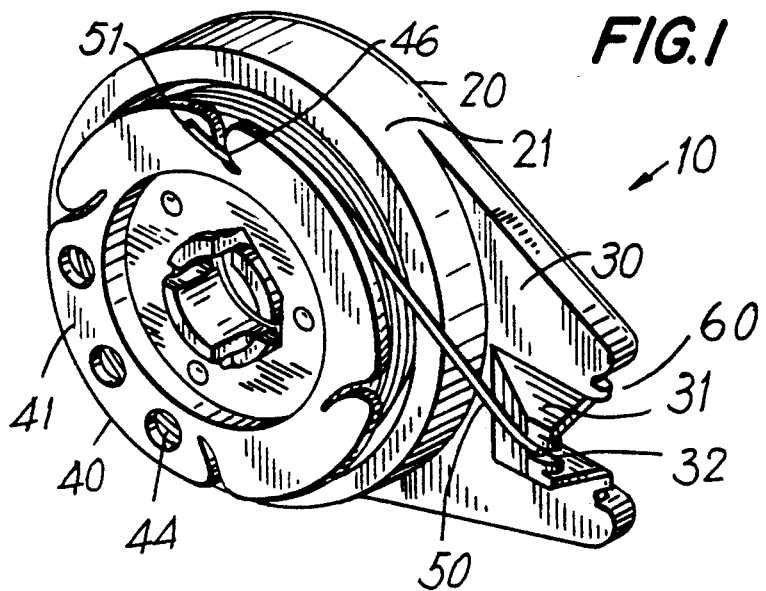
Figure 2:
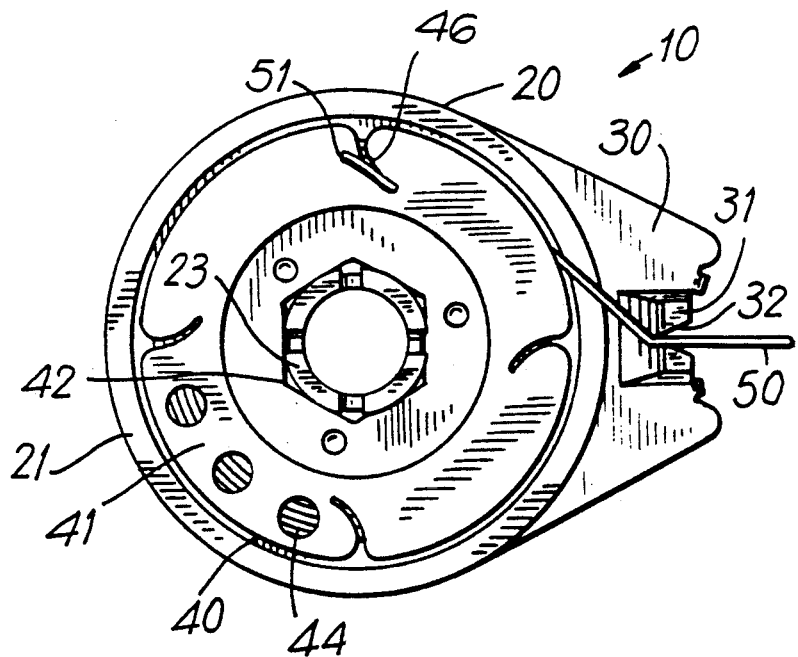
Figure 3:
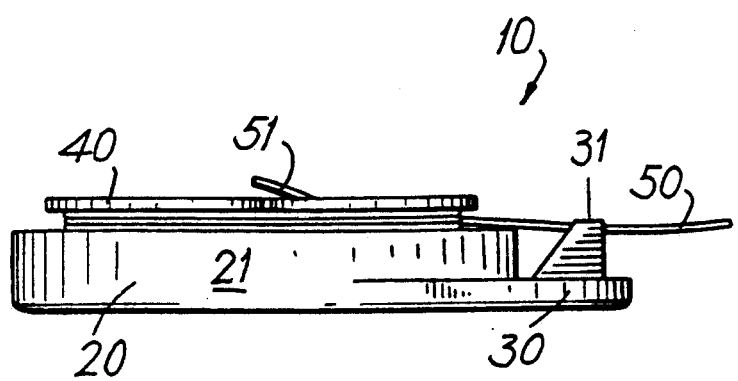
Figure 4:
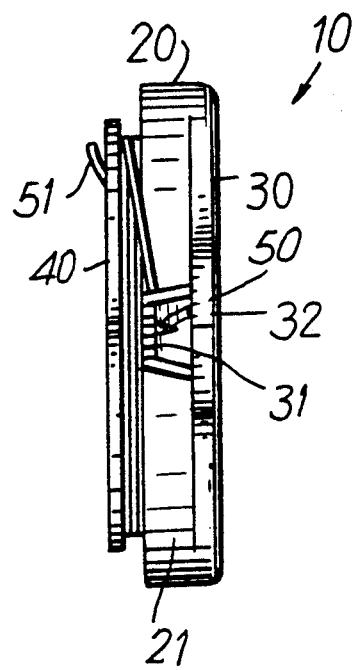
Figure 5:
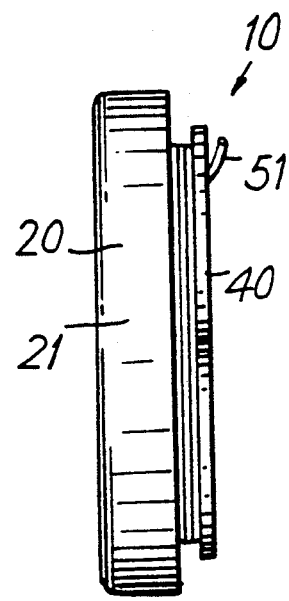

As shown in FIGS 1-10, suture dispenser 10 possesses a receptacle component 20 of circular configuration for receiving suture-dispensing reel 40. Receptacle 20 possesses an extension member 30 of approximately trapezoidal configuration with suture-retaining slotted member 31 projecting outwardly therefrom at one end. The components of suture dispenser 10 can be fabricated from any suitable material and are advantageously formed by injection molding an injection moldable thermoplastic resin, e.g., a polyolefin such as polyethylene or polypropylene, a polyester such as polyethylene terephthalate, etc. Reel 40 is advantageously formed from a transparent or semi-transparent resin for better visibility of suture 50 wound thereon.

Figure 6:
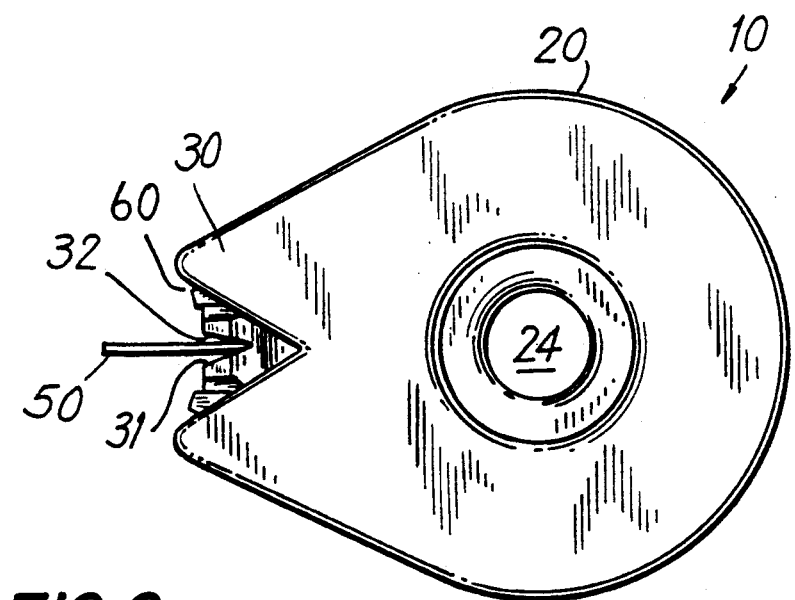

As best viewed in FIG. 7, receptacle 20 possesses a circumferential wall 21 defining a well 22. The inside diameter of well 22 is preferably only slightly larger than the outside diameter of suture-dispensing reel 40. A concentrically disposed flanged hub 23 with opening 24 is raised slightly from the base, or floor, 25 of well 22 by platform 26 to provide clearance with rim 41 of reel 40. Extension member 30 is provided as a linear extension of floor 25 of receptacle 20. Outwardly projecting suture-retaining slotted member 31 possesses a v-shaped slot 32 which serves to retain suture 50 once a desired length of suture has been played out from reel 40. The relative heights of circumferential wall 21 and slotted member 31 are advantageously so arranged that suture 50 will make no, or at most occasional or only slight, contact with the top of wall 21 as it is dispensed from the reel. In the embodiment of suture dispenser 10, this is achieved by making the height of slotted member 31 just greater than the height of wall 21. As shown in FIGS. 1, 6, and 7, extension member 30 preferably is configured with a recess 60. Recess 60 facilitates placement and removal of the suture strand in v-shaped slot 32 without interference.

Reel 40 possesses an axial bore 42, hexagonally shaped to facilitate its snap-fit with hub 23 of receptacle 20. Hub 23 is advantageously provided with a slight flange 28 to better retain reel 40 once the latter is snapped into place within well 22 of receptacle 20. Notches 27 are provided on hub 23 to take up the slight compression which occurs when reel 40 is snap-fitted in place. Platform 26 raises rim 45 of reel 40 slightly above floor 25 of receptacle 20 so that reel 40 can rotate more freely about hub 23. If desired, reel 40 can be provided with hole(s) 44 the number of which correspond to the suture size. Thus, in the embodiment shown, three holes designate a size 3/0 suture. Of course, other indicia can be provided for this purpose. Arcuate notches 46 which are evenly distributed along rim 41 of reel 40 serve as alternate engagement points for a knotted end 51 of suture 50 which is thereafter wound to its full length, e.g., from about 36 to about 120 inches or more, and preferably from about 50 to about 100 inches, upon the reel.

After suture 50 has been wound on reel 40 and reel 40 snap fitted in place within well 22 of receptacle 20, the assembled dispenser is sterilized and packaged in the sterile state. To dispense a length of suture from the dispenser, the unit is held comfortably but securely in one hand, the desired length of suture is withdrawn from the reel with the other hand and at the approximate terminal point of the length of withdrawn suture, the suture is retained under moderate tension in slot 32 on member 31. The suture may then be cut in the vicinity of slot 32 to provide the desired length of suture.

While the above description of the suture dispenser of this invention contains many specifics, these specifics should not be construed as limitations on the scope of the invention, but merely as exemplifications of preferred embodiments thereof. Those skilled in the art will envision many other possible variations of the suture dispenser that are within the scope and spirit of the invention as defined by the claims appended hereto.

What is claimed:

1. A suture dispenser possessing a cylindrically shaped receptacle having a top and a bottom, a suture-dispensing reel rotatably seated within the receptacle, an extension member connected to a section of the receptacle, and a suture-retaining slotted member positioned upon the extension member and projecting upwardly therefrom in the direction of the reel axis for retaining the suture unwound from the reel in a slot formed therein, wherein the reel is seated within the receptacle such that an entire upper rim thereof clears the top of the receptacle and the suture is arranged to pass over the top of the receptacle to the slotted member for retention within the slotted member.

2. The suture dispenser of claim 1 wherein relative height of the receptacle from top to bottom and upward projection of the suture-retaining slotted member are arranged so that the suture makes only occasional contact with the top of the receptacle upon being withdrawn therefrom.

3. The dispenser of claim 1 wherein the upward projection of the suture-retaining slotted member is greater than height of the receptacle from to top to bottom so that the suture makes only occasional contact with the top of the receptacle upon being withdrawn therefrom.

4. The suture dispenser of claim 1 wherein the suture-retaining slotted member possesses a V-shaped suture-retaining slot.

5. The suture dispenser of claim 1 wherein the suture-retaining reel is fabricated from a transparent or semi-transparent thermoplastic resin.

6. The suture dispenser of claim 1 wherein the peripheral surface of the reel is free from contact with the adjacent surface of the receptacle.

7. The suture dispenser of claim 1 wherein the receptacle possesses a flanged hub for securing the suture-dispensing reel thereto.

8. The suture dispenser of claim 1 wherein the receptacle possesses a hub with one or more notches for taking up the laterally compressive force which is applied to the hub when the suture-dispensing reel is fitted thereto.

9. The suture dispenser of claim 7 wherein the hub possesses one or more notches for taking up the laterally compressive force which is applied to the hub when the suture-dispensing reel is fitted thereto.

10. The suture dispenser of claim 1 possessing means for identifying the size of suture stored therein.

11. The suture dispenser of claim 1 possessing one or more holes on the reel, the number of holes corresponding to the size of the suture wound on the reel.

12. The suture dispenser of claim 1 wherein the receptacle possesses a platform for raising the reel slightly above a floor of the receptacle.

* * * * *